(12) United States Patent
Kong et al.

(10) Patent No.: US 11,834,428 B2
(45) Date of Patent: Dec. 5, 2023

(54) DIHYDROMYRICETIN NANOCRYSTALS AND PREPARATION METHOD AND APPLICATION THEREOF

(71) Applicant: Shaanxi University of Science and Technology, Xi'an (CN)

(72) Inventors: Yang Kong, Xi'an (CN); ChangZhao Wang, Xi'an (CN); Bin Tian, Xi'an (CN); Fang Lin, Xi'an (CN); Zihao Li, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 18/116,204

(22) Filed: Mar. 1, 2023

(65) Prior Publication Data
US 2023/0286935 A1    Sep. 14, 2023

(30) Foreign Application Priority Data
Mar. 8, 2022    (CN) .......................... 202210227200.5

(51) Int. Cl.
*C07D 311/30*    (2006.01)

(52) U.S. Cl.
CPC ........ *C07D 311/30* (2013.01); *C07B 2200/13* (2013.01)

(58) Field of Classification Search
CPC .......................... C07D 311/30; C07B 2200/13
See application file for complete search history.

(56) References Cited

FOREIGN PATENT DOCUMENTS

| CN | 104496955 A | 4/2015 | |
| CN | 108670953 A * | 10/2018 | ............. A23L 29/00 |
| CN | 112028865 A | 12/2020 | |

OTHER PUBLICATIONS

CN108670953A 2018 WIPO English machine translation, p. 1-22.*
Jahangir, M.A."Nanocrystals: Characterization overview, applications in drug delivery, and their toxicity concerns." Journal of Pharmaceutical Innovation (2022):17:237-248; published online Sep. 28, 2020.*
Wang Jian et al., "Recent progress of nanocrystal technology in increasing the dissolution and bioavailability of poorly water soluble drugs", Journal of Shenyang Pharmaceutical University, Mar. 2016, pp. 253-258, vol. 33, No. 3.
CNIPA, Notification of a First Office Action for CN202210227200.5, dated Sep. 30, 2022.
Shaanxi University of Science and Technology (Applicant), Reply to Notification of a First Office Action for CN202210227200.5, w/ replacement claims, dated Nov. 28, 2022.
Shaanxi University of Science and Technology (Applicant), Supplemental Reply to Notification of a First Office Action for CN202210227200.5, w/ (allowed) replacement claims, dated Nov. 28, 2022.
CNIPA, Notification to grant patent right for invention in CN202210227200.5, dated Dec. 12, 2022.

* cited by examiner

*Primary Examiner* — John M Mauro
(74) *Attorney, Agent, or Firm* — Zhigang Ma

(57) ABSTRACT

A method for preparing dihydromyricetin nanocrystals includes: uniformly dispersing dihydromyricetin in a good solvent to obtain a dihydromyricetin solution; uniformly dispersing a precipitator and a stabilizer in water to obtain a mixed solution, and then adding the dihydromyricetin solution into the mixed solution and mixing uniformly under a stirring condition to obtain a dihydromyricetin nanocrystal solution; and drying the dihydromyricetin nanocrystal solution to obtain the dihydromyricetin nanocrystals. The method for preparing the dihydromyricetin nanocrystals by an anti-solvent method is simple and easy to implement, low in cost, good in nanocrystal stability, small in organic solvent consumption, and safe and environment-friendly in preparation process.

2 Claims, 2 Drawing Sheets

DIHYDROMYRICETIN NANOCRYSTALS AND PREPARATION METHOD AND APPLICATION THEREOF

TECHNICAL FIELD

The disclosure relates to the technical field of pharmaceutical preparations, and more particularly to dihydromyricetin nanocrystals, a method for preparing dihydromyricetin nanocrystals and an application of dihydromyricetin nanocrystals.

BACKGROUND

Nanoparticles generally refer to nanoparticles with particle sizes of about 1~1000 nanometer (nm). Nanoparticles in drugs can generally include drug nanocrystals and drug-loaded nanoparticles. Drug nanocrystals are prepared by directly processing and mixing drugs with various grades into nano-drug crystals with various nano-shapes, sizes, and different scales, and then processing these nano-drug crystals into a suitable nano-drug preparation for clinical application of drugs.

Characteristics of nanocrystal drugs are as follows.

(a) The absorption of oral administration of poorly water-soluble drugs is effectively improved: after the nanocrystal drug is dissolved in a solvent, the drug can be directly decomposed and crushed, and finally the nanosuspension is prepared, which is suitable for direct taking through oral administration, injection and other ways, so as to greatly increase the bioavailability of drugs.

(b) The retention time of drugs in the body is increased: after nano-carriers are subject to surface modification by hydrophilic materials such as polyethylene glycol and other macromolecular compound, nanocrystal drugs can escape from the endothelial system in vivo, which is beneficial to decrease the exposure time of drugs in the process of circulation in vivo, thus greatly increasing the retention time of drugs in vivo, and further increasing the drug efficacy.

(c) The ability of drugs to directly pass through capillaries and brain nerve barriers in the patient's brain is effectively improved: the concentration of drugs in the patient's brain can be effectively improved and the clinical effectiveness can be increased.

(d) The targeting effect of drugs is improved: by controlling the particle size of drugs, which organs and tissues of the human body the drugs are concentrated in can be controlled, thus achieving the goal of targeted therapy, which greatly increases the bioavailability of drugs, reduces the consumption of other drugs in unnecessary organs and tissues, and further greatly reduces the adverse reactions of drugs.

(e) Nanomaterials can be used as specific carriers of various biological macromolecular drugs: these types of nano-carriers have good chemical activity, can promote the absorption of various microorganisms in human body, and have stability and targeting effect in vivo.

Dihydromyricetin (DMY, $C_{15}H_{12}O_8$) is widely found in a variety of health foods with homology of medicine and food, such as Semen Hoveniae (also referred to as Hovenia Dulcis or raisin tree seed), Vine tea, etc. The dihydromyricetin has many physiological activities, such as alcohol detoxication, liver protection, anti-fatigue, blood lipid regulation, anti-tumor, anti-inflammatory and antigenic microorganisms. It has the effects of treating alcoholism, preventing alcoholic liver and fatty liver, inhibiting the deterioration of liver cells, reducing the incidence rate of liver cancer, anti-fatigue, anti-inflammation, analgesia and bacteriostasis. The dihydromyricetin, as a promising drug for relieving alcoholism and protecting liver, has attracted people's attention, but its clinical application is limited due to its low bioavailability and poor druggability. In order to improve the bioavailability of the dihydromyricetin, it is of great significance to provide dihydromyricetin nanocrystals, a method for preparing dihydromyricetin nanocrystals and an application of dihydromyricetin nanocrystals.

SUMMARY

In order to solve the problems of poor water solubility and low bioavailability of the dihydromyricetin, dihydromyricetin nanocrystals, a method for preparing dihydromyricetin nanocrystals and an application of dihydromyricetin nanocrystals are provided. As the average particle size of the dihydromyricetin nanocrystals is less than or equal to 300 nanometers (nm), the dihydromyricetin nanocrystals can be well dissolved in water, ethanol and other solvents, thus the absorption of oral administration of the poorly water-soluble drug dihydromyricetin can be effectively improved, the absorption is fast, and the bioavailability is good.

In a first aspect, a method for preparing dihydromyricetin nanocrystals is provided, including the following steps:

uniformly dispersing the dihydromyricetin in a good solvent to obtain a dihydromyricetin solution; and uniformly dispersing a precipitator and a stabilizer in water to obtain a mixed solution, adding the dihydromyricetin solution into the mixed solution and then uniformly mixing under a stirring condition to obtain a dihydromyricetin nanocrystal solution, and drying the dihydromyricetin nanocrystal solution to obtain the dihydromyricetin nanocrystals.

In an embodiment, the good solvent is at least one selected from a group consisting of ethanol, ethyl acetate, n-butanol and acetone; and a dosage ratio of the dihydromyricetin to the good solvent is 50 milligrams (mg): 1 milliliter (mL).

In an embodiment, the precipitator is at least one selected from a group consisting of water, chloroform and petroleum ether.

In an embodiment, the stabilizer is sodium dodecyl sulfate or Tween-80 (also referred to as polysorbate 80).

In an embodiment, a volume ratio of the precipitator to the Tween-80 is 1~4:0.1; or a dosage ratio of the precipitator to the sodium dodecyl sulfate is 1~4 mL: 0.1 mg.

In a second aspect, dihydromyricetin nanocrystals are provided, particle sizes of the dihydromyricetin nanocrystals are less than or equal to 300 nm.

In a third aspect, an application of dihydromyricetin nanocrystals in preparing a drug for antibiosis, quick-acting alcohol detoxication, antioxidation, anti-cancer or liver protection is provided.

Compared with the prior art, the beneficial effects of the disclosure are as follows.

The dihydromyricetin nanocrystals provided by the disclosure take the dihydromyricetin as the model drug, one or more of ethanol, methanol, ethyl acetate, n-butanol and acetone as the good solvent, one or more of water, chloroform and ethyl acetate as the precipitant, one of sodium dodecyl sulfate and Tween-80 as the stabilizer, and the dihydromyricetin nanocrystals are prepared by the precipitation method. The precipitation method utilizes the chemical properties that the dihydromyricetin has high solubility in good solvents such as absolute ethanol and the like and is difficult to dissolve in solvents such as purified water and the like at room temperature, takes a small amount of the good solvent such as absolute ethanol and the like as a dissolving agent, takes the purified water and the like as a precipitator, and takes the particle size of a nanocrystal suspension as an index to screen an appropriate stabilizer, a stirring speed, a volume ratio of the good solvent to the precipitator, a preparation temperature, a drug concentration and the like to prepare the dihydromyricetin nanocrystals. The method is simple and easy to implement, low in cost, good in nanocrystal stability, small in organic solvent consumption, and safe and environment-friendly in preparation process.

The dihydromyricetin nanocrystals provided by the disclosure solve the problem of low solubility of the drug itself, effectively improve the absorption of dihydromyricetin by oral administration, and the prepared dihydromyricetin nanocrystal suspension can be directly taken by oral administration, injection, and other ways, so that the bioavailability of the drug is greatly increased.

The dihydromyricetin nanocrystals provided by the disclosure are beneficial to decrease the exposure time of the drug in the process of circulation in vivo, thus increasing the retention time of the drug in vivo and further increasing the drug efficacy.

The average particle size of dihydromyricetin nanocrystals provided by the disclosure is less than or equal to 100 nm. By controlling the particle size of drugs, the goal of targeted therapy is achieved, which greatly increases the availability of drugs, reduces the consumption of other drugs in unnecessary organs and tissues, and greatly reduces the adverse reactions of drugs.

The dihydromyricetin nanocrystals provided by the disclosure can be used as specific carriers for various biological macromolecular drugs, can promote the absorption of various human microorganisms, and have stability and targeting effect in vivo.

DETAILED DESCRIPTION OF EMBODIMENTS

In order to enable those skilled in the art to better understand the technical solution of the disclosure and implement the technical solution of the disclosure, the disclosure will be further described in combination with specific embodiments, but the embodiments given are not intended to limit the disclosure.

It should be noted that experimental methods in the following embodiments are conventional methods unless otherwise specified. Reagents and materials used can be purchased on the market unless otherwise specified.

Embodiment 1

A method for preparing dihydromyricetin nanocrystals includes the following steps.

50 milligrams (mg) of dihydromyricetin active pharmaceutical ingredient (API) is weighed, 1 milliliter (mL) of absolute ethanol is added into the dihydromyricetin API, and then the dihydromyricetin API is fully dissolved by magnetic stirring at 800 revolution per minute (r/min) for 10 minutes at 25° C. to obtain a first solution (also referred to as dihydromyricetin solution). 8 mL of purified water and 0.2 mL of Tween-80 (also referred to as polysorbate 80) are taken, and fully stirred to obtain a second solution (also referred to as mixed solution). The first solution is dropped into the second solution under a stirring condition, and then the stirring is continued for 20 minutes to obtain a dihydromyricetin nanocrystal solution. After drying of the dihydromyricetin nanocrystal solution, the dihydromyricetin nanocrystals are obtained.

Figure 1:
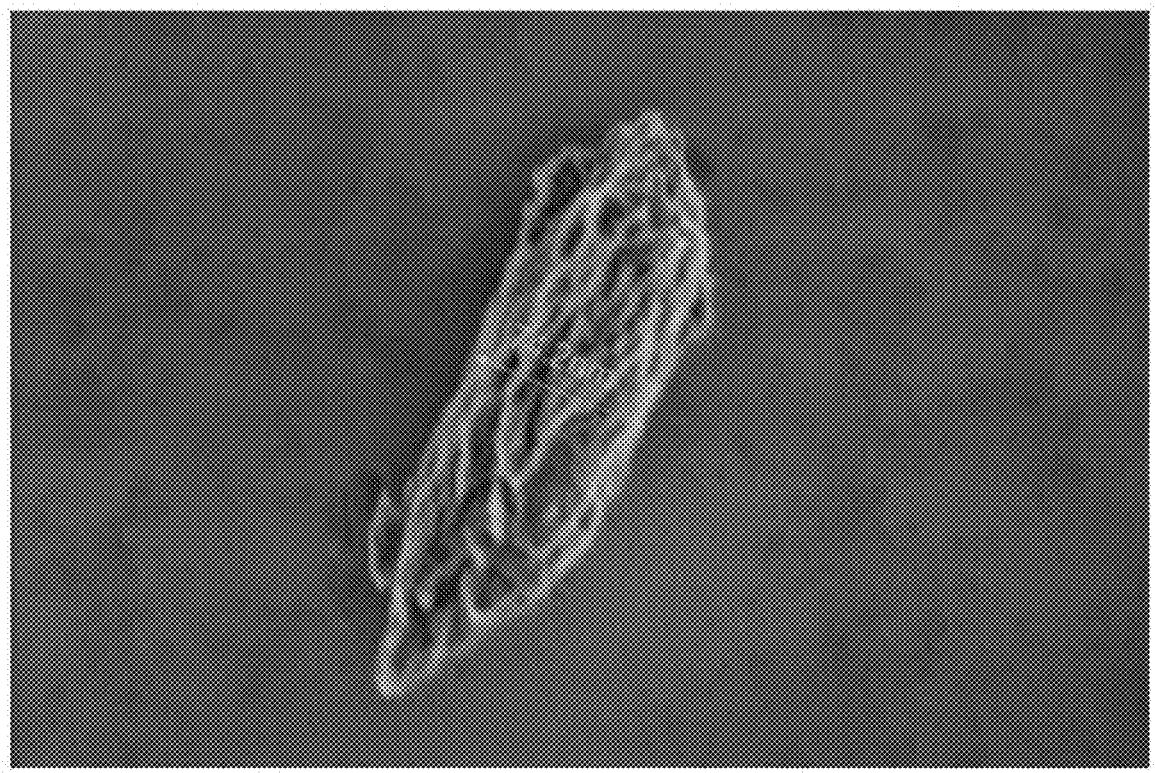
FIG. 1 illustrates a scanning electron microscope image of a dihydromyricetin nanocrystal according to an embodiment 1.

In this embodiment, (1) the absolute ethanol is used as a good solvent, the purified water is used as a precipitator, and the dihydromyricetin nanocrystals are prepared by an anti-solvent method. As shown in FIG. 1, the nanocrystals have uniform particle size and are not easy to aggregate. (2) The average particle size of the nanocrystals is less than or equal to 100 nanometers (nm), and the dihydromyricetin nanocrystals have good solubility and high biocompatibility.

Embodiment 2

A method for preparing dihydromyricetin nanocrystals includes the following steps.

50 mg of dihydromyricetin API is weighed, 1 mL of absolute ethanol is added into the dihydromyricetin API, and then the dihydromyricetin API is fully dissolved by magnetic stirring at 800 r/min for 10 minutes at 25° C. to obtain a first solution. 8 mL of chloroform and 0.2 mL of Tween-80 are taken, and fully stirred to obtain a second solution. The first solution is dropped into the second solution under a stirring condition, and then the stirring is continued for 20 minutes to obtain a dihydromyricetin nanocrystal solution. After drying of the dihydromyricetin nanocrystal solution, the dihydromyricetin nanocrystals are obtained.

In this embodiment, compared with the embodiment 1, (1) the chloroform is used as a precipitator, and the prepared nanocrystals have good solubility and stability; (2) the nanocrystals have uniform particle size and are not easy to aggregate, and the average particle size is less than or equal to 300 nm.

Embodiment 3

A method for preparing dihydromyricetin nanocrystals includes the following steps.

50 mg of dihydromyricetin API is weighed, 1 mL of absolute ethanol is added into the dihydromyricetin API, and then the dihydromyricetin API is fully dissolved by magnetic stirring at 800 r/min for 10 minutes at 25° C. to obtain a first solution. 4 mL of purified water and 0.2 mL of sodium dodecyl sulfate (SDS) are taken, and fully stirred to obtain a second solution. The first solution is dropped into the second solution under a stirring condition, and then the stirring is continued for 20 minutes to obtain a dihydromyricetin nanocrystal solution. After drying of the dihydromyricetin nanocrystal solution, the dihydromyricetin nanocrystals are obtained.

In this embodiment, compared with the embodiment 1, (1) the sodium dodecyl sulfate is used as a stabilizer, the prepared nanocrystals have good solubility and stability; (2)

the nanocrystals have uniform particle size and are not easy to aggregate, and the average particle size is less than or equal to 300 nm.

Embodiment 4

A method for preparing dihydromyricetin nanocrystals includes the following steps.

50 mg of dihydromyricetin API is weighed, 1 mL of absolute ethanol is added into the dihydromyricetin API, and then the dihydromyricetin API is fully dissolved by magnetic stirring at 800 r/min for 10 minutes at 25° C. to obtain a first solution. 4 mL of purified water and 0.2 mL of Tween-80 are taken, and fully stirred to obtain a second solution. Then, 0.8 mL (containing 10 mg dihydromyricetin) of the first solution is sucked with a dropper and slowly added into the second solution, and fully stirred for 20 minutes to obtain a dihydromyricetin nanocrystal solution. After drying of the dihydromyricetin nanocrystal solution, the dihydromyricetin nanocrystals are obtained.

In this embodiment, compared with the embodiment 1, (1) the purified water is used as a precipitator, the prepared nanocrystals have good solubility and stability; (2) the nanocrystals have uniform particle size and are not easy to aggregate, and the average particle size is less than or equal to 100 nm.

Embodiment 5

A method for preparing dihydromyricetin nanocrystals includes the following steps.

50 mg of dihydromyricetin API is weighed, 1 mL of absolute ethanol is added into the dihydromyricetin API, and then the dihydromyricetin API is fully dissolved by magnetic stirring at 800 r/min for 10 minutes at 25° C. to obtain a first solution. 2 mL of purified water and 0.2 mL of Tween-80 are taken, and fully stirred to obtain a second solution. Then, 0.4 mL (containing 10 mg dihydromyricetin) of the first solution is sucked with a dropper and slowly added into the second solution, and fully stirred for 20 minutes to obtain a dihydromyricetin nanocrystal solution. After drying of the dihydromyricetin nanocrystal solution, the dihydromyricetin nanocrystals are obtained.

In this embodiment, compared with the embodiment 4, (1) the purified water is used as a precipitator, the prepared nanocrystals have good solubility and stability; (2) the nanocrystals have uniform particle size and are not easy to aggregate, and the average particle size is less than or equal to 400 nm.

Embodiment 6

A method for preparing dihydromyricetin nanocrystals includes the following steps.

50 mg of dihydromyricetin API is weighed, 1 mL of absolute ethanol is added into the dihydromyricetin API, and then the dihydromyricetin API is fully dissolved by magnetic stirring at 500 r/min for 10 minutes at 25° C. to obtain a first solution. 8 mL of purified water and 4 mL of Tween-80 are taken, and fully stirred to obtain a second solution. The first solution is slowly dropped into the second solution under a stirring condition, and then the stirring is continued for 20 minutes to obtain a dihydromyricetin nanocrystal solution. After drying of the dihydromyricetin nanocrystal solution, the dihydromyricetin nanocrystals are obtained.

In this embodiment, compared with the embodiment 1, (1) the stirring speed is 500 r/min, the stirring time is constant, and the stability of the obtained dihydromyricetin nanocrystals is good; (2) the nanocrystals have uniform particle size and are not easy to aggregate, and the average particle size is less than or equal to 300 nm.

Comparative Embodiment 1

A method for preparing dihydromyricetin nanocrystals includes the following steps.

50 mg of dihydromyricetin API is weighed, 1 mL of absolute ethanol is added into the dihydromyricetin API, and then the dihydromyricetin API is fully dissolved by magnetic stirring at 800 r/min for 10 minutes at 25° C. to obtain a first solution. 8 mL of purified water is taken, the first solution is slowly dropped into the purified water under a stirring condition, and then the stirring is continued for 20 minutes to obtain a dihydromyricetin nanocrystal solution. After drying of the dihydromyricetin nanocrystal solution, the dihydromyricetin nanocrystals are obtained.

In this comparative embodiment 1, the absolute ethanol is used as a good solvent, the purified water is used as a precipitator, a stabilizer is not added, and the dihydromyricetin nanocrystals is prepared by an anti-solvent method. The prepared nanocrystal particles have uneven diameter and aggregation phenomenon. The particle size distribution of the nanocrystals is not uniform, with 20% of the nanocrystals less than or equal to 300 nm, 60% of the nanocrystals greater than or equal to 300 nm and less than or equal to 1000 nm, and 20% of the nanocrystals greater than or equal to 1000 nm. The nanocrystals have poor stability, are easy to aggregate and increase in particle size.

Comparative Embodiment 2

A method for preparing dihydromyricetin nanocrystals includes the following steps.

50 mg of dihydromyricetin API is weighed, 2 mL of methanol and 0.2 mL of Tween-80 are added into the dihydromyricetin API, and then the dihydromyricetin API is fully dissolved by magnetic stirring at 800 r/min for 10 minutes at 25° C. to obtain a first solution. 8 mL of chloroform is taken, the first solution is slowly dropped into the chloroform under a stirring condition, and then the stirring is continued for 20 minutes.

In this comparative embodiment 2, the methanol is used as a good solvent, the chloroform is used as a precipitator, and the Tween-80 is used as a stabilizer. It is easy to produce flocculent precipitation after adding the precipitator, and the particle sizes of the nanocrystals prepared after fully stirring are not uniform, and the aggregation phenomenon is relatively serious. The content of nanocrystals is small, only 20% of the nanocrystals is less than or equal to 600 nm, and the other 80% of the nanocrystals greater than 1000 nm. The nanocrystals have poor stability, are easy to aggregate and increase in particle size.

The above comparative embodiments indicate that when the stabilizer is not added or the chloroform is used as the precipitator, the prepared dihydromyricetin nanocrystals have uneven particle size, poor stability, easy aggregation into micron-sized crystals, reduced solubility and failure to meet the requirements of nanocrystals.

In order to describe the dihydromyricetin nanocrystals provided by the disclosure, the relevant properties of the embodiments 1 to 6 and the comparative embodiments are measured.

1. The Effect of Stabilizers on the Particle Size and Solubilization Effect of the Dihydromyricetin Nanocrystals, See Table 1.

TABLE 1

Effect of stabilizers on the particle size and solubilization effect of dihydromyricetin nanocrystals

| Sample | Particle size | Stabilizer | Solubility in cold water (mg/mL) |
| --- | --- | --- | --- |
| Dihydromyricetin nanocrystals | 600 nm~1000 nm | / | 5.0 |
|  | ≤100 nm | Tween-80 | 60 |
|  | ≤300 nm | sodium dodecyl sulfate (SDS) | 38 |
| Dihydromyricetin API | ≥12 μm | / | 0.04 |
|  |  | Tween-80 | 0.6 |
|  |  | SDS | 0.3 |

It can be seen from the Table 1 that the stabilizer has a great influence on the particle size and solubility of dihydromyricetin. By adding the stabilizer Tween-80, the particle size of dihydromyricetin nanocrystals can be significantly reduced and the solubility in cold water can be improved.

2. Product Stability

The nanocrystals provided in the embodiment 1 are used, and its content is determined after one week of storage, the recovery rate is calculated, and the distribution of the nanocrystals is observed under electron microscope. See Table 2 and FIG. 2.

TABLE 2

Stability results of dihydromyricetin nanocrystals provided in the embodiment 1

| Addition amount | Measured after one week | Recovery rate |
| --- | --- | --- |
| 50.22 | 50.19 | 99.94 |

Figure 2:
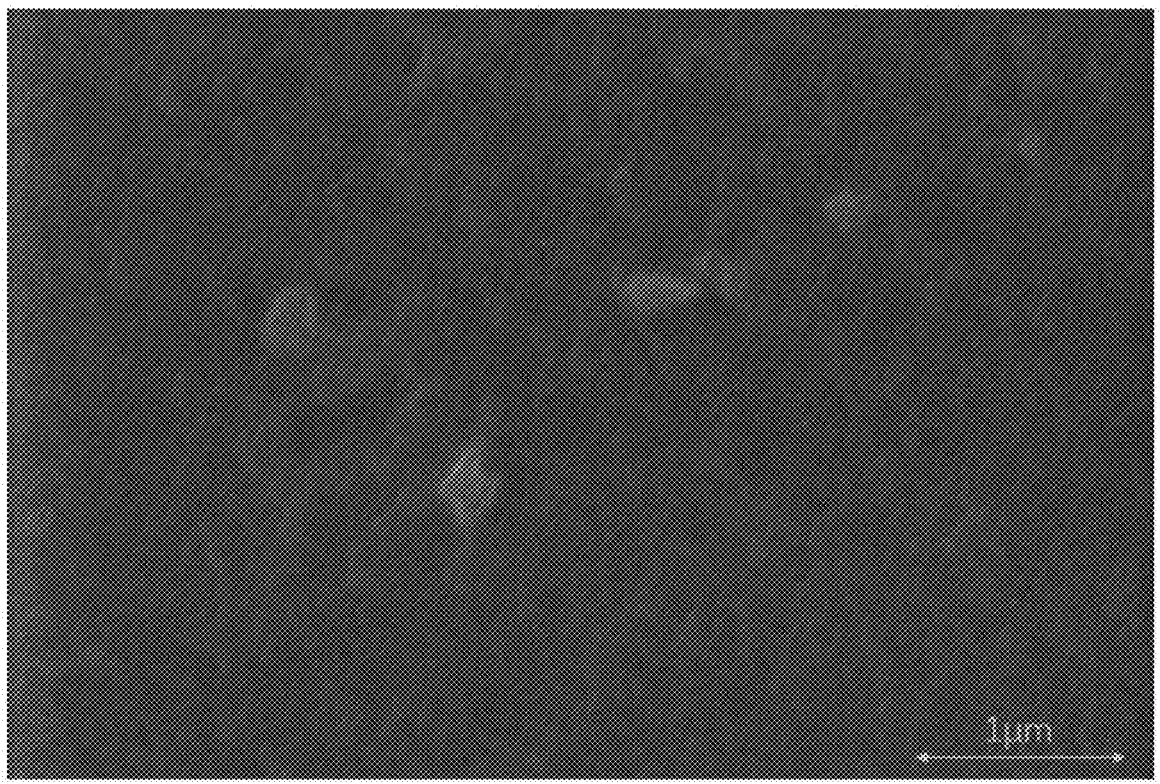
FIG. 2 illustrates a high-resolution field emission scanning electron microscope image of the dihydromyricetin nanocrystal according to the embodiment 1 after one week.
Figure 3:
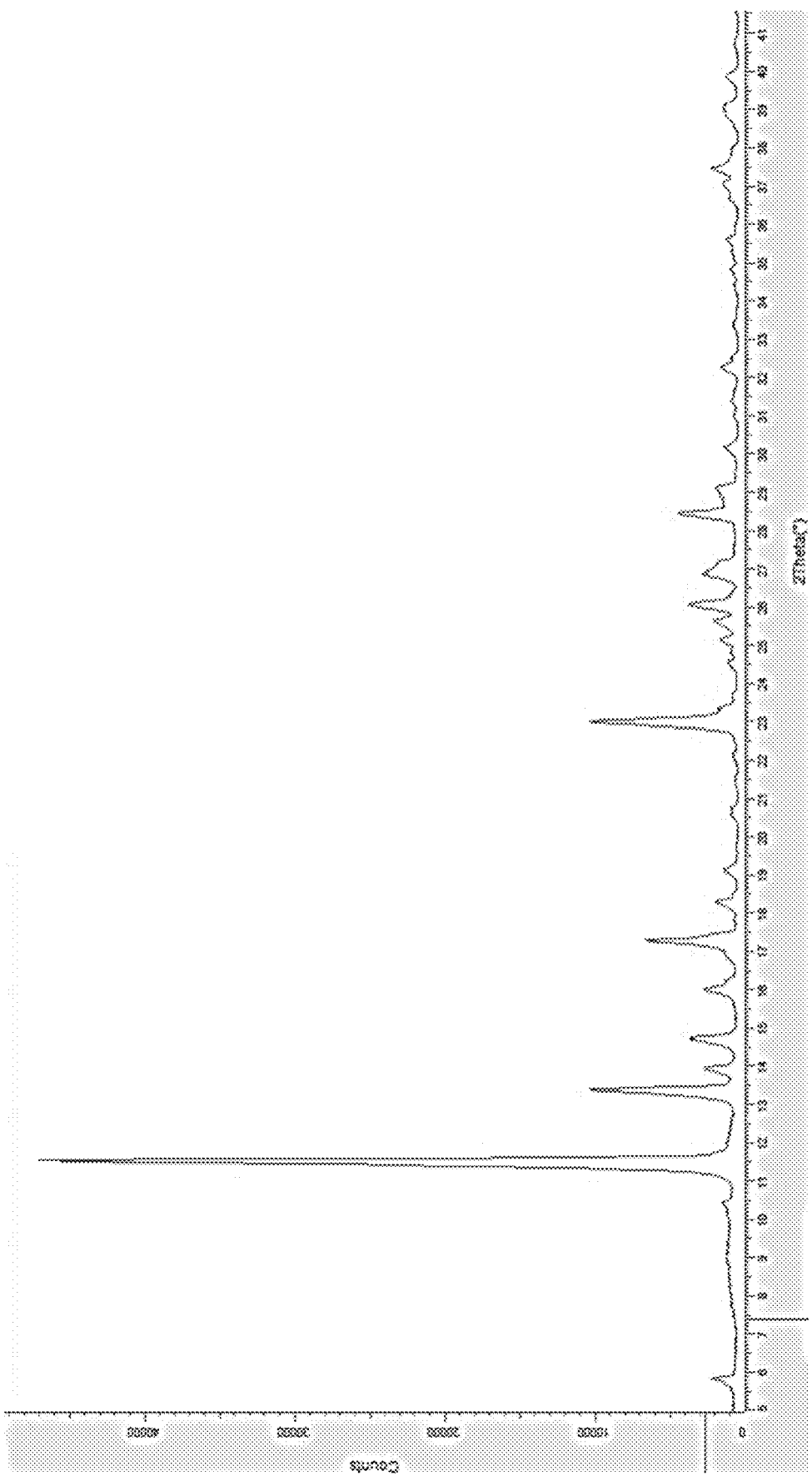
FIG. 3 illustrates an X-ray diffraction (XRD) pattern of the dihydromyricetin nanocrystals, where crystal diffraction peaks are found at 11.5, 13.41, 14.71, 15.98, 17.30, 18.28, 23.03, 28.48, indicating that the test sample of dihydromyricetin is crystals.

FIG. 2 is a high-resolution field emission scanning electron microscope image of the nanocrystals provided in the embodiment 1 after one week of storage.

As can be seen from Table 2 and FIG. 2, the recovery rate is measured to be 99.94% after the nanocrystals are placed for one week. Under the high-resolution field emission scanning electron microscope, it is observed that the dihydromyricetin nanocrystals are still nanoparticles at room temperature for one week, with uniform distribution and good stability. Storage conditions should be dry and cool.

In conclusion, the dihydromyricetin nanocrystals provided by the disclosure make up for the low solubility of the drug itself, solve the problems of poor water solubility and low bioavailability of dihydromyricetin, and dihydromyricetin nanocrystals and the method for preparing dihydromyricetin nanocrystals and the application of dihydromyricetin nanocrystals are provided. The average particle size of the nanocrystals is less than or equal to 300 nm, which can be well dissolved in water, ethanol and other solvents, thus the absorption of oral administration of the poorly water-soluble drug dihydromyricetin can be effectively improved, the absorption is fast, and the bioavailability is good.

The dihydromyricetin nanocrystals provided by the disclosure take the dihydromyricetin as the model drug, one or more of ethanol, methanol, ethyl acetate, n-butanol and acetone as the good solvent, one or more of water, chloroform and ethyl acetate as the precipitant, one of sodium dodecyl sulfate and Tween-80 as the stabilizer, and the dihydromyricetin nanocrystals are prepared by the anti-solvent precipitation method.

The average particle size of the preparation is less than or equal to 100 nm, the solubility is high, the drug release speed is high, and the absorption of oral administration of the dihydromyricetin is effectively improved. The prepared dihydromyricetin nanocrystal suspension can be directly taken by oral administration, injection, and other ways, so that the bioavailability of the drug is greatly increased.

The method for preparing dihydromyricetin nanocrystals provided by the disclosure is simple and easy to implement, low in cost, good in nanocrystal stability, small in organic solvent consumption, and safe and environment-friendly in preparation process.

The dihydromyricetin nanocrystals provided by the disclosure can be used as specific carriers for various biological macromolecular drugs, can promote the absorption of various human microorganisms, and has stability and targeting effect in vivo.

The disclosure utilizes the chemical properties that the dihydromyricetin (DMY) has high solubility in good solvents such as absolute ethanol and the like and is difficult to dissolve in solvents such as purified water and the like at room temperature, takes a small amount of the good solvents such as absolute ethanol and the like as a dissolving agent, takes the purified water and the like as a precipitator, and takes the particle size of a nanocrystal suspension as an index to screen an appropriate stabilizer, a stirring speed, a volume ratio of the good solvent to the precipitator, a preparation temperature, a drug concentration and the like to prepare the dihydromyricetin nanocrystal suspension. When using the anti-solvent method to prepare dihydromyricetin nanocrystals, appropriate stabilizers that have no effect on the film formation should be selected, so that the dihydromyricetin drug solution slowly drops into the film formation solution and precipitates into uniform nanometer particles, and the appropriate temperature should be set when drying the film to avoid the precipitation of drug crystals.

The disclosure describes preferred embodiments and their effects. However, those skilled in the art can make additional changes and modifications to these embodiments once they know the basic creative concepts. Therefore, the appended claims are intended to be interpreted as including preferred embodiments and all changes and modifications falling within the scope of the disclosure.

Although the embodiments of the disclosure have been illustrated and described, those skilled in the art can understand that these embodiments can be varied, modified, substituted, and changed without departing from the principle and spirit of the disclosure. The scope of the disclosure is limited by the appended claims and their equivalents.

What is claimed is:

1. A method for preparing dihydromyricetin nanocrystals solid preparation, comprising:
uniformly dispersing dihydromyricetin in a good solvent to obtain a dihydromyricetin solution;
uniformly dispersing a precipitator and a stabilizer in water to obtain a mixed solution, and adding the dihydromyricetin solution into the mixed solution and then mixing uniformly under a stirring condition to obtain a target solution; and
drying the target solution to obtain the dihydromyricetin solid preparation comprising the stabilizer and dihydromyricetin nanocrystals;
wherein particle sizes of the dihydromyricetin nanocrystals are less than or equal to 300 nanometers (nm);

wherein the good solvent is at least one selected from a group consisting of ethanol, ethyl acetate, n-butanol and acetone; and a dosage ratio of the dihydromyricetin to the good solvent is 50 milligrams (mg): 1 milliliter (mL);

wherein the stabilizer is one of sodium dodecyl sulfate and Tween-80, and a volume ratio of the precipitator to the one of the sodium dodecyl sulfate and the Tween-80 is 1~4 mL: 0.1 mg;

wherein the precipitator is at least one selected from a group consisting of water, chloroform and petroleum ether.

2. A method for preparing dihydromyricetin solid preparation of nanoscale dimensions, comprising:

uniformly dispersing dihydromyricetin in a good solvent to obtain a dihydromyricetin solution;

uniformly dispersing a precipitator and a stabilizer in water to obtain a mixed solution, and adding the dihydromyricetin solution into the mixed solution and then mixing uniformly under a stirring condition to obtain a target solution; and drying the target solution to obtain the dihydromyricetin solid preparation comprising the stabilizer and dihydromyricetin nanoparticles; wherein particle sizes of the dihydromyricetin nanoparticles are less than or equal to 300 nanometers (nm);

wherein a dosage ratio of the dihydromyricetin to the good solvent is 50 mg: 1 mL;

wherein a volume ratio of the precipitator to the stabilizer is 1~4 mL: 0.1 mg.

\* \* \* \* \*